(12) United States Patent
Parker

(10) Patent No.: US 7,459,042 B2
(45) Date of Patent: Dec. 2, 2008

(54) METHOD OF LOADING EXPANDABLE MEDICAL DEVICE IN A LOW VAPOR ENVIRONMENT

(75) Inventor: Fred T. Parker, Unionville, IN (US)

(73) Assignee: Cook Incorporated, Bloomington, IN (US)

( * ) Notice: Subject to any disclaimer, the term of this patent is extended or adjusted under 35 U.S.C. 154(b) by 546 days.

(21) Appl. No.: 11/351,815

(22) Filed: Feb. 10, 2006

(65) Prior Publication Data

US 2006/0196073 A1    Sep. 7, 2006

Related U.S. Application Data

(60) Provisional application No. 60/652,314, filed on Feb. 11, 2005.

(51) Int. Cl.
*C22F 1/10* (2006.01)
(52) U.S. Cl. .................................. 148/676; 148/712
(58) Field of Classification Search ....................... None
See application file for complete search history.

(56) References Cited

U.S. PATENT DOCUMENTS 5,554,181 A * 9/1996 Das ........................... 623/1.12
6,083,257 A * 7/2000 Taylor et al. ................ 623/1.46
6,823,576 B2 * 11/2004 Austin ........................... 29/516
6,837,901 B2 * 1/2005 Rabkin et al. ............... 623/1.11
2002/0051730 A1 * 5/2002 Bodnar et al .................. 422/33
2002/0138126 A1 * 9/2002 Camrud et al. ............. 623/1.11
2003/0070469 A1 * 4/2003 Kokish ......................... 72/402
2005/0166389 A1 * 8/2005 Perreault et al. .............. 29/508

FOREIGN PATENT DOCUMENTS

WO    WO-01/32104 A1 *  5/2001

OTHER PUBLICATIONS

International Search Report and Written Opinion in PCT/US2006/004886, filed Feb. 10, 2006.*

* cited by examiner

*Primary Examiner*—George Wyszomierski
(74) *Attorney, Agent, or Firm*—Richard J. Godlewski

(57) ABSTRACT

A method (112) of loading an expandable medical device in a low vapor environment. The method includes placing the device in a loading chamber (114) at, for example, room temperature and removing (116) from the chamber any undesirable contaminants such as water vapor that can form condensation on the device when the device is cooled for compression into a transfer tube or delivery catheter. The temperature in the chamber is lowered (118) to a temperature below the transition temperature (martensitic finish) of the device. The device is compressed (120) below its' transition temperature and loaded (122) into a delivery or transfer device.

10 Claims, 12 Drawing Sheets

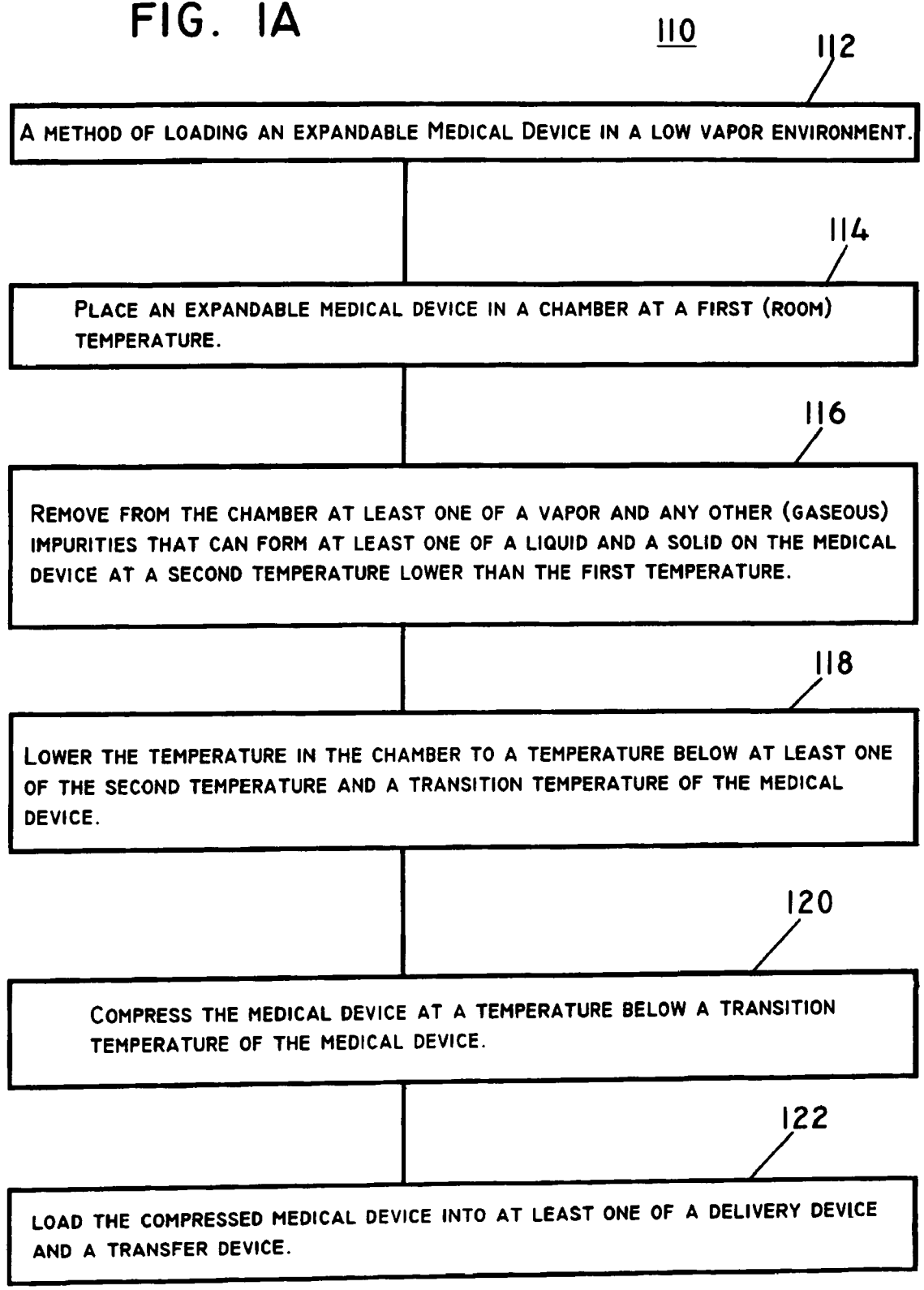

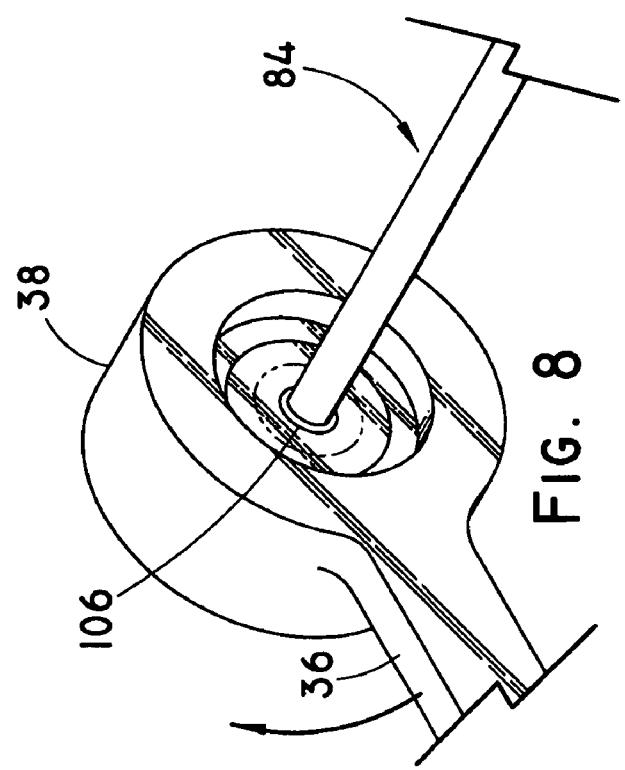
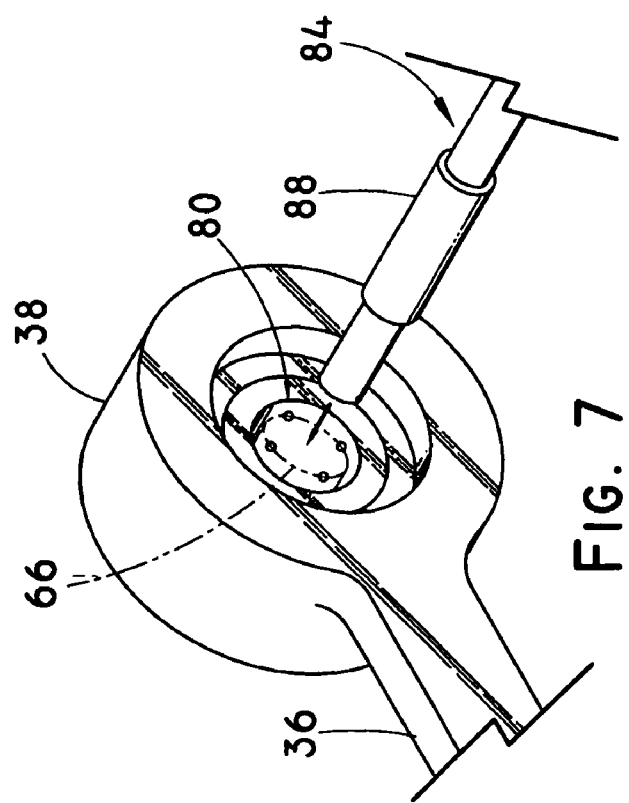

METHOD OF LOADING EXPANDABLE MEDICAL DEVICE IN A LOW VAPOR ENVIRONMENT

CROSS-REFERENCE TO RELATED APPLICATIONS

This application claims priority of provisional application Ser. No. 60/652,314, filed Feb. 11, 2005.

TECHNICAL FIELD

This invention relates generally to medical devices, and, in particular, to a method of loading an expandable medical device.

BACKGROUND OF THE INVENTION

Various expandable implantable medical devices such as stents, bone clips, vena cava filters, etc., are most easily and safely inserted into a passageway of the body such as the vascular system if they are first compressed into a small diameter configuration, then inserted into the body and expanded. Stents, for example, are compressed to fit onto or into a delivery catheter, which is then inserted into the body vessel such as a coronary artery, then expanded and released or released and expanded.

Because the catheter and stent must travel through the patient's vasculature, the stent must have a small delivery diameter and must be firmly secured within a delivery catheter until the physician is ready to implant it. Thus, the stent must be loaded onto or into the delivery catheter so that it does not interfere with delivery, and it must not come off the catheter until it is implanted.

In procedures where a self-expanding medical device such as a stent is utilized, the stent is placed within a protective delivery sleeve of the delivery catheter. It is necessary to properly collapse or compress the stent for loading it into the protective delivery sleeve. This collapsing or compressing of the stent has proven to be a particular challenge where it is necessary to load the stent into a small diameter delivery catheter.

In one loading procedure, a self-expanding stent is compressed to a small diameter and then inserted into a transfer tube. The compressed self-expanding stent is then loaded into a delivery sleeve of the delivery catheter by pushing the compressed self-expanding stent from the transfer tube into the protective delivery sleeve. This loading procedure is completed by connecting a tapered dilator head to the distal end of the delivery catheter by, for example, positioning the distal tip on a central rod or tube that extends through the longitudinal passageway of the loaded stent.

Several commercially available stent crimping or compression devices are available, which uniformly compress a self-expanding stent from a fully expanded state to a much smaller diameter compressed state for insertion into a transfer tube or delivery catheter.

Many vascular medical procedures further require the placement of a coated implantable medical device into the body of the patient. The placement of a metal or polymeric device however, gives rise to numerous complications. In particular, the placement of a bare expandable, implantable medical device such as a stent causes trauma to the vascular wall resulting often times in hyperplasia and restenosis of the vessel with the proliferation of smooth muscle cells at the implantation site.

One approach to reducing the potential harmful effects of such an introduction is to provide a coated, expandable, implantable medical device such as a stent having a coating of a bioactive material such as an antiproliferative that is delivered with the stent at the implantation site. By so doing, the harmful effects associated with implantation can be diminished. In particular, bioactive compounds such as paclitaxel and other antiproliferative materials are applied to the surface of the stent. These antiproliferative materials come in contact with the vessel wall and inhibit, among others, hyperplasia and restenosis of the vessel.

This bioactive coating material along with the stent must be reduced to a small diameter for loading onto a delivery catheter. This loading procedure is often further complicated when the stent such as a nitinol stent must be cooled to temperatures below the martensitic start and final temperatures of the nitinol material prior to compression and insertion into the delivery catheter. This is done to reduce the force necessary to load nitinol stents into an insertion or delivery catheter. Because the nitinol stent is completely martensitic, it is pliable and ductile, and easily compressed for loading into a delivery catheter. However, cooling a nitinol stent with a bioactive material coating thereon presents additional loading problems.

Nitinol stents are typically placed in a cooling chamber or container in which the temperature of the stent is reduced to below its martensitic final temperature such as, for example, below −40 degrees C. After the fully expanded nitinol stent is cooled to below its martensitic final temperature, it is then positioned in a stent crimper or compression apparatus and uniformly compressed to a much smaller diameter size for loading into the delivery sheath of a delivery catheter. However, the stent compression apparatus is typically at a temperature below the austenitic start temperature of the nitinol stent. Depending upon the environmental conditions of the cooling chamber, water or ice as well as other condensates or sublimates, often form on the compression apparatus as well as the coated nitinol stent. This condensation or sublimates can adversely affect the operation of the compression device as well as form an additional layer or thickness on the surface of the coated nitinol stent. The condensate or sublimate can significantly affect the compression of the stent so that the coated stent cannot be easily pushed into a transfer tube or a delivery sheath of the delivery catheter. The condensate or sublimate can be water or ice crystals formed from water vapor or crystals formed from the sublimation of carbon dioxide gas. Other condensates and sublimates such as oxygen and other contaminants found, in, for example, the air, are contemplated.

SUMMARY OF THE INVENTION

The foregoing problems are solved and a technical advance is achieved in an illustrative method of loading an expandable, implantable medical device such as a coated, self-expanding nitinol stent into a delivery or transfer device such as a delivery catheter or transfer tube. The method includes the steps of placing the expandable medical device in a loading chamber at for example room temperature and removing from the chamber any undesirable contaminants including water vapor and carbon dioxide gas that are purged from the loading chamber during the removal step to minimize, if not eliminate, condensation or sublimates in the chamber and on the device when the coated nitinol stent is, for example, cooled for the purpose of compression into a transfer tube or delivery catheter. The temperature in the chamber is then lowered to a temperature at least below the transition temperature of the device such as the martensitic start temperature or more preferably the martensitic finish temperature of the nitinol. At the lowered temperature, the medical device is compressed and then loaded into the transfer tube or delivery catheter.

The step of removing the undesirable contaminants includes purging the chamber with a gas such as nitrogen gas for a minimum amount of time.

The step of lowering the temperature in the chamber includes the step of lowering the temperature at a rate slow enough to remove the contaminants before condensation or sublimination can occur.

The step of lowering the temperature in the chamber can also advantageously include introducing liquid nitrogen into the chamber, heating the liquid nitrogen to form nitrogen gas and then lowering the temperature in the chamber with the nitrogen gas.

The method also includes inserting the medical device in compression fixture. The step of compression includes inserting the medical device at a temperature below its' transition temperature into the compression fixture and then compressing the medical device from a first diameter to a second smaller diameter without advantageously any contaminants having formed on the medical device.

Without any contaminants having formed on the medical device, the device is advantageously loaded or transferred to a transfer tube or delivery catheter without the contaminants interfering with the loading step.

BRIEF DESCRIPTION OF THE DRAWING

FIG. 1A depicts a block diagram flow chart of the present invention of a method of loading an expandable medical device in a low vapor environment;

FIG. 7 depicts a diagram of an expanded medical device of the present invention inserted into a radial compressor with the mandril of FIGS. 5 and 6.

FIG. 8 depicts a diagram of a compressed expandable stent in the radial compressor compressing the stent on a support mandril inserted through the lumen of the medical device;

DETAILED DESCRIPTION

Figure 1B:
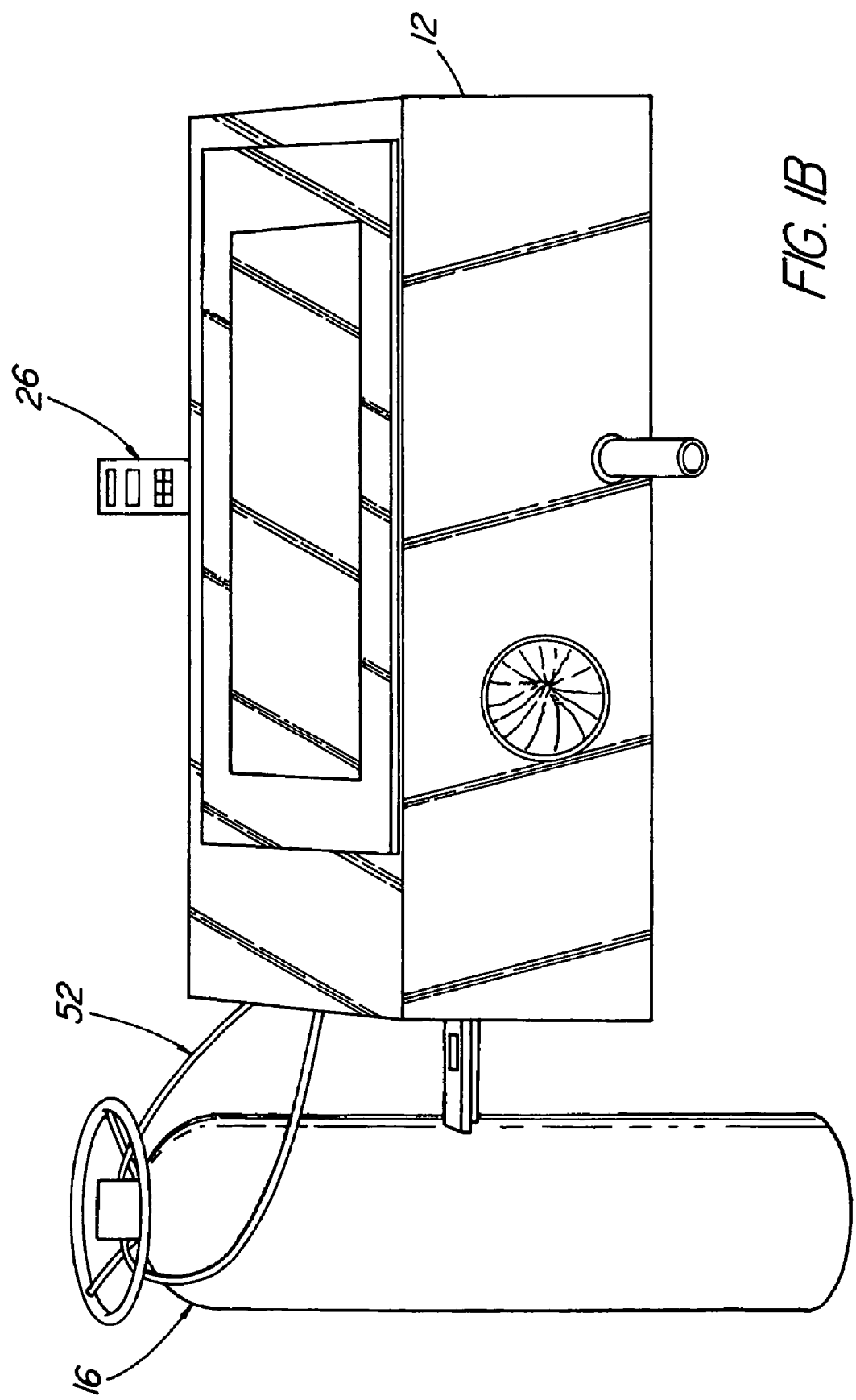
FIG. 1B is a photograph of a loading chamber of the present invention in which an expandable medical device is inserted therein and its temperature lowered for loading into a delivery or transfer device.

FIG. 1A depicts a block diagram flow chart 110 of the present invention including a method 112 of loading an expandable medical device in a low vapor environment. The method 112 includes the step of placing an expandable medical device in a cooling chamber at a first room temperature as depicted in block 114. Another step as depicted in block 116 includes removing from the chamber at least one of a vapor and any other gaseous impurity that can form at least one of a liquid and a solid on the medical device at a second temperature lower than the first temperature. Still another step as depicted in block 118 includes lowering the temperature in the chamber to a temperature below at least one of the second temperature and a transition temperature such as the martensitic start temperature of for example a nitinol medical device. The method further includes the step as depicted in block 120 of compressing the medical device at a temperature below the transition temperature of the medical device. Lastly as depicted in block 122 of the flow chart diagram, the method includes the step of loading the compressed medical device into the delivery device or a transfer tube.

FIG. 1B is a photograph of a commercially available loading chamber 12 with a commercially available liquid nitrogen source 16 attached thereto. Nitrogen gas evacuater 52 is positioned on one side of the chamber next to the nitrogen source while a temperature read out gauge 26 measures the temperature inside the loading chamber and in particular the Dewar vessel 40. Also shown in the photograph is a flow meter, a viewing window, a stent delivery tube, a stent access tube on the front of the chamber, and an air cylinder and an adjustment knob for controlling the flow of air into the chamber.

Figure 1C:
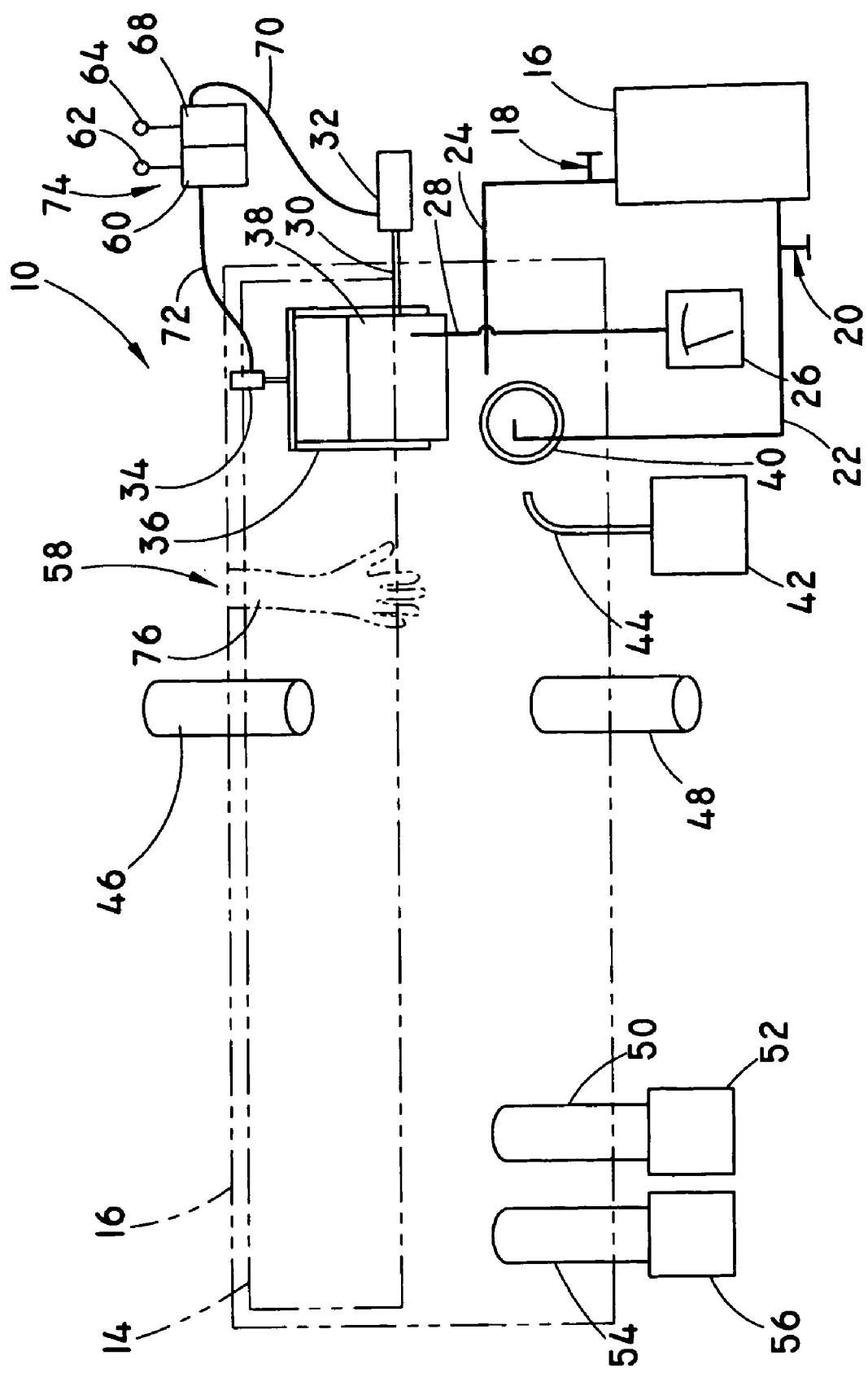
FIG. 1C depicts a schematic diagram of the loading chamber into which an expandable medical device is loaded into a delivery or transfer device.

FIG. 1C depicts a schematic diagram of the loading chamber 12 of the present invention in which an expandable medical device 66 is inserted into the chamber and the temperature of the chamber and device is lowered for loading into a delivery or transfer device 94.

Figure 2A:
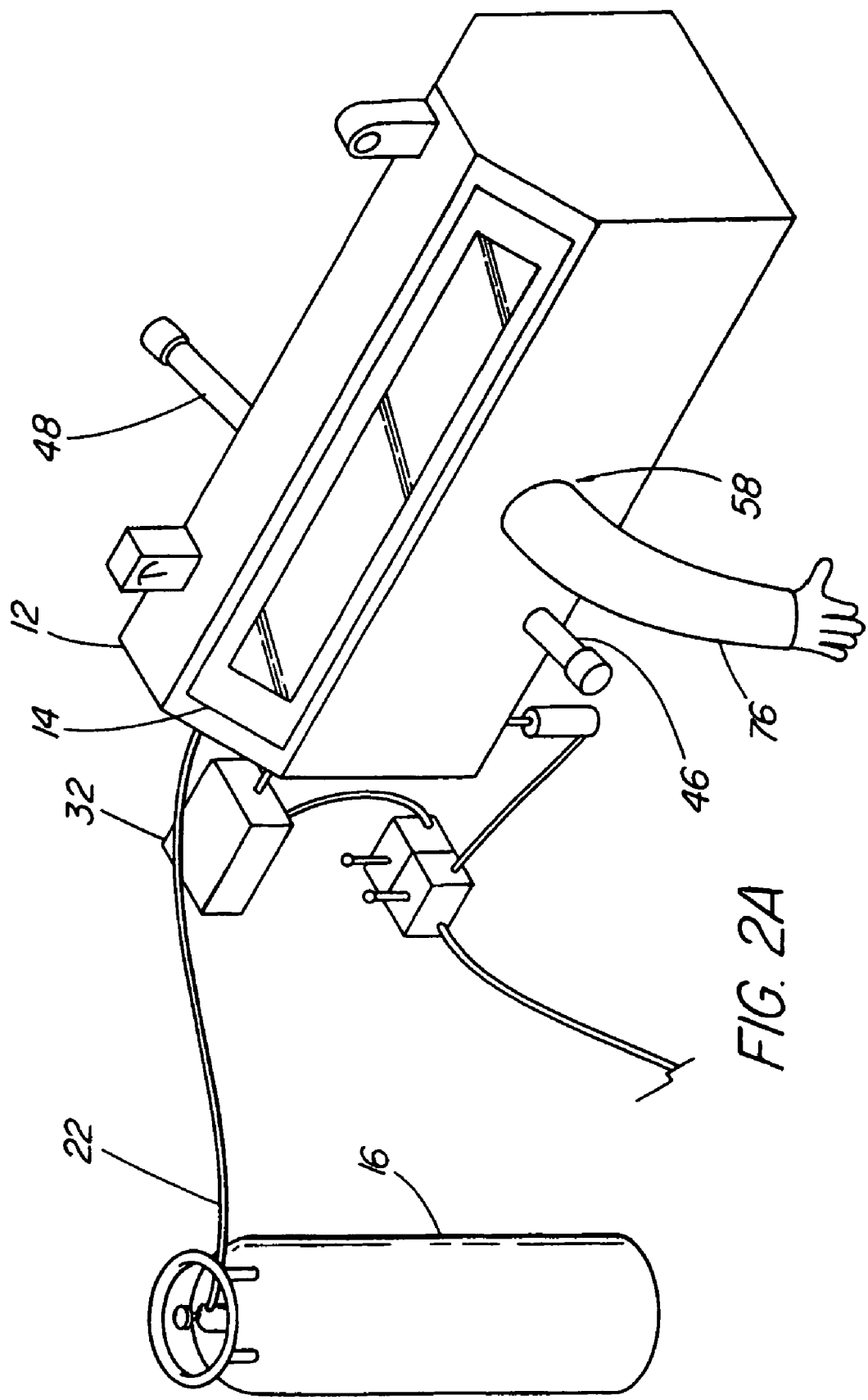
FIG. 2A depicts a simplified pictorial schematic of the loading chamber apparatus of the present invention of FIG. 1C.

FIG. 2A depicts a simplified schematic diagram of the loading chamber 12 of the present invention of FIG. 1C. Connected to the loading chamber is a liquid nitrogen source 16 which supplies liquid nitrogen to the chamber via line 22. A cannula pusher device 32 is positioned at one end of the loading chamber for pushing the expandable medical device into a transfer tube from a compressor which will be described hereinafter. An access door 14 is provided at the front of the cooling chamber for viewing and gaining access into the interior of the chamber. A stent container access tube 46 and stent delivery tube 48 are positioned on the front and back of the cooling chamber. Manipulation of the device is provided by manipulator device 76 such as a insulated sleeve and glove which is inverted for access into the chamber.

Figure 2B:
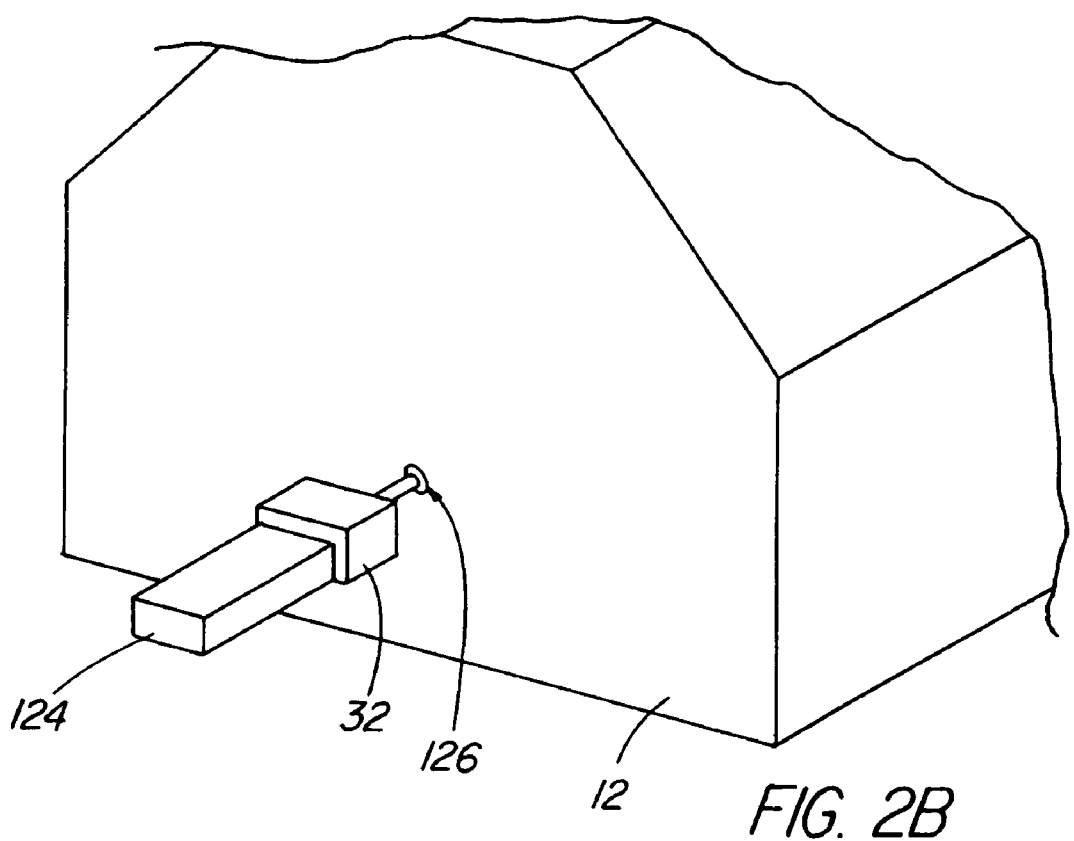
FIG. 2B is an end photographic view of the loading chamber of FIG. 1B.

FIG. 2B is an end photographic view of the loading chamber of FIG. 1B in which a force gauge 124 is shown positioned on one end of loading chamber 12 with a seal 126 around the cannula pusher 32.

Figure 2C:
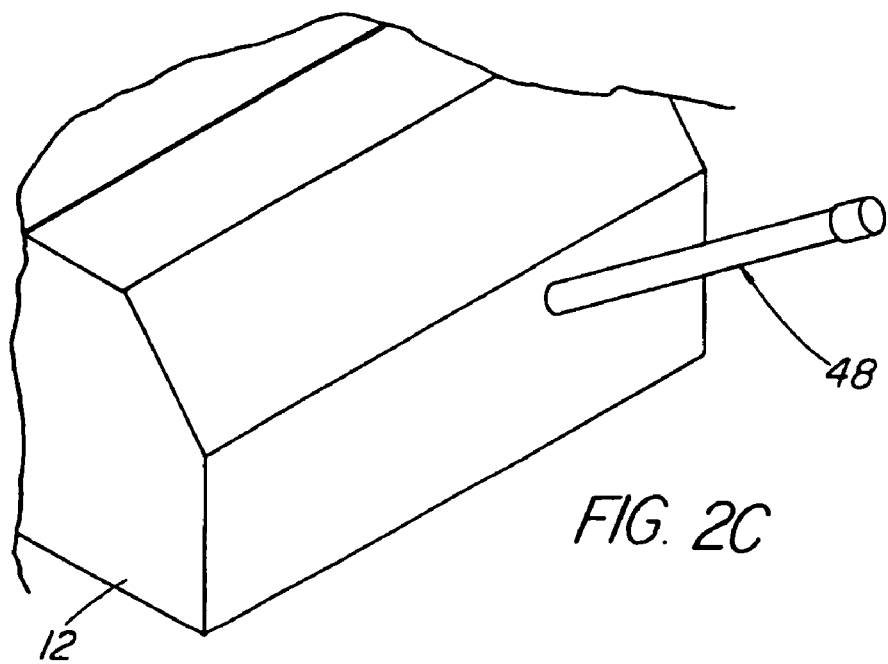
FIG. 2C is a back photographic view of the loading chamber of FIG. 1B.

FIG. 2C is a photographic view of the back of the loading chamber of FIG. 1B with access tube 48 for inserting stents into the chamber.

Figure 3A:
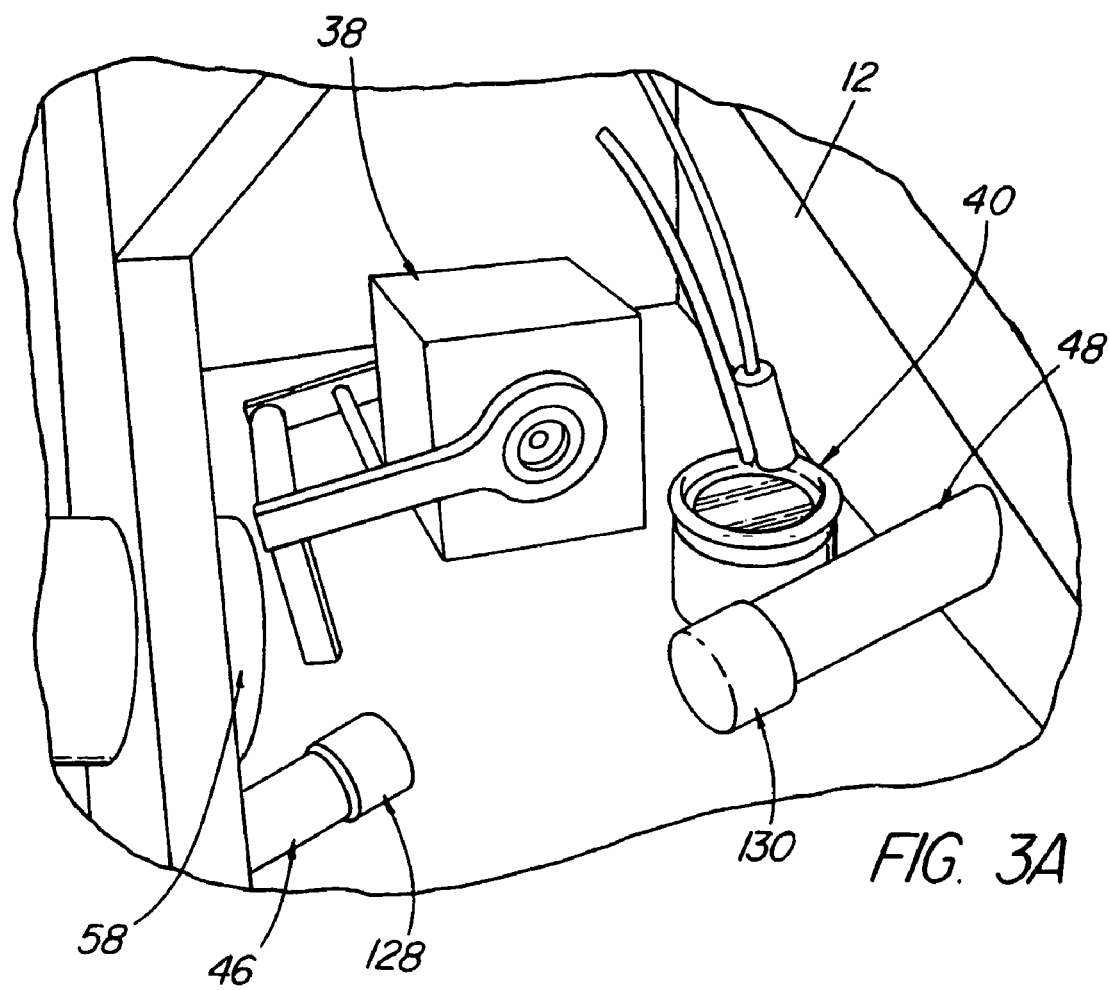
FIG. 3A is a photograph of the interior of the loading chamber of FIG. 1B.

FIG. 3A is a photographic view of the interior of the loading chamber 12 with stent delivery tube 48 extending therein. Air lock caps 128 and 130 are respectively positioned on outlet tube 46 and inlet access tube 48. Glove access port 58 is shown at the front of the interior chamber. Compression fixture 38 is shown in the interior of the loading chamber next to liquid nitrogen container 40 known commonly as a Dewar vessel.

Figure 3C:
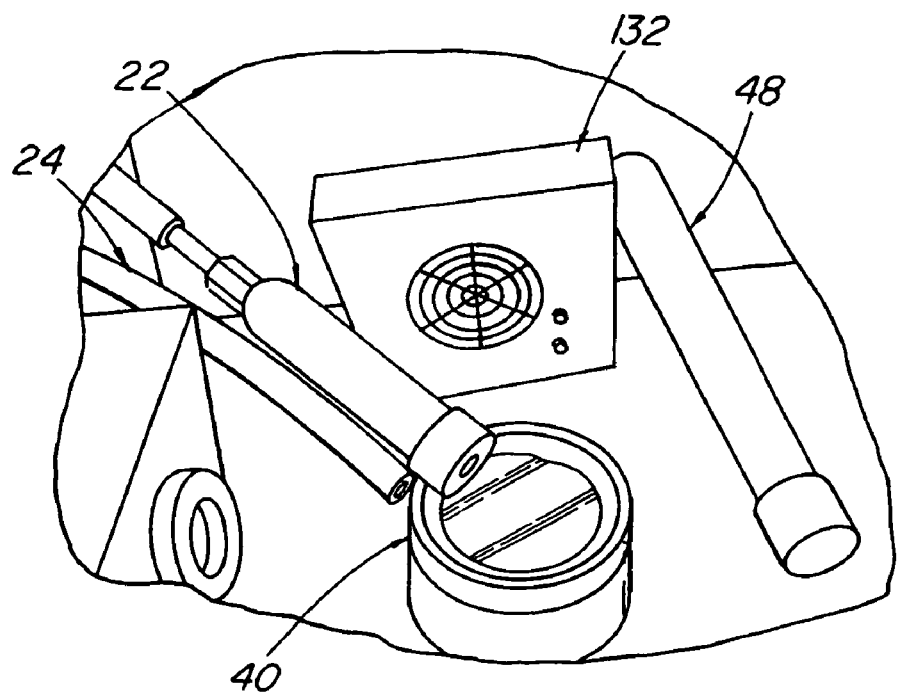
FIG. 3C is an enlarged photograph of the interior of the loading chamber of FIG. 3A.
Figure 3B:
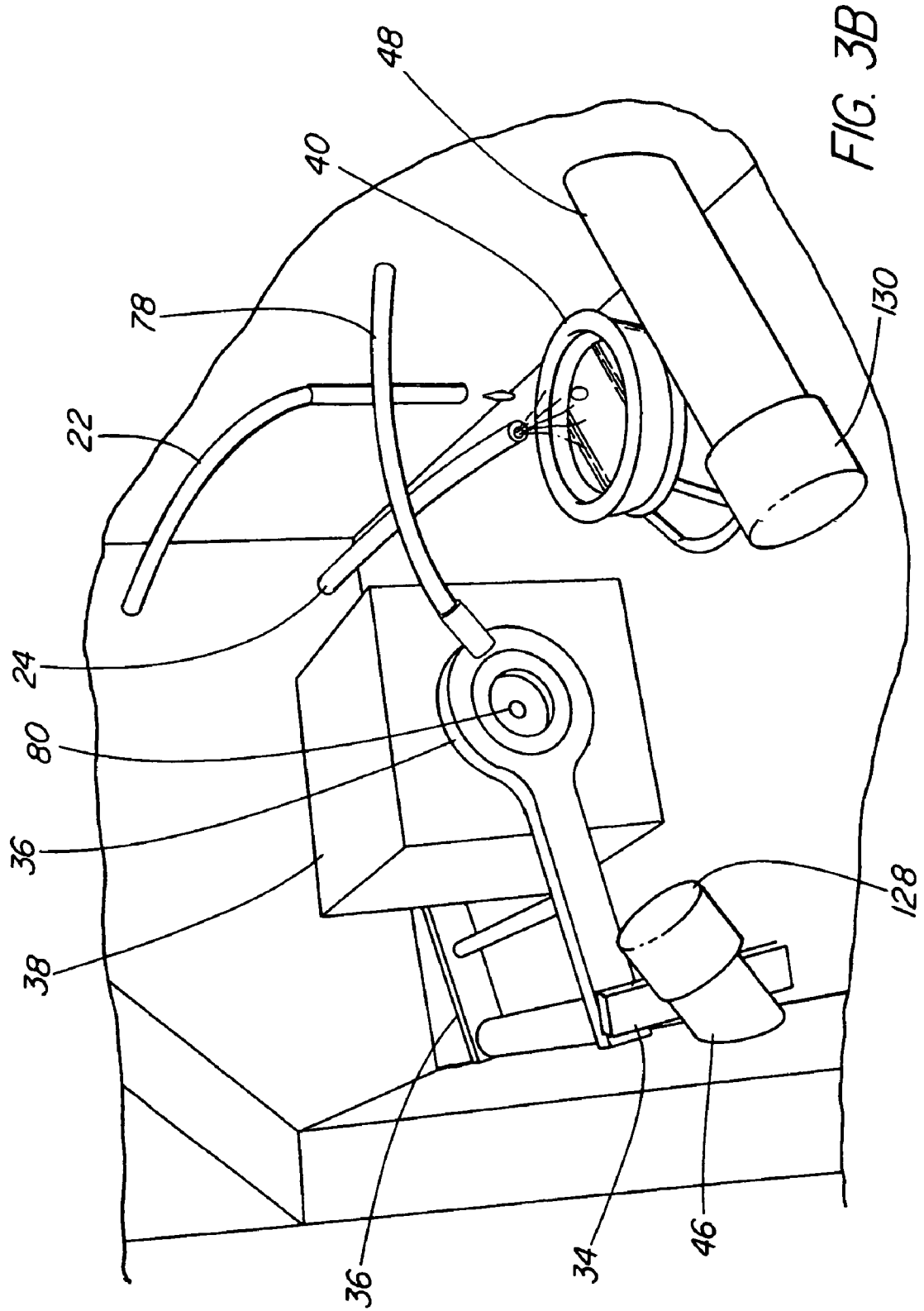
FIG. 3B is a partial diagram of the interior of the loading chamber of FIG. 1C.

FIG. 3B is an enlarged partial diagram of the interior of the loading chamber of FIG. 1C that further depicts the photograph of FIG. 3A. In addition to stent compressor 38 as previously described, stent compressor actuator cylinder 34 and actuator arm 36 open and close collet opening 80 in which the expandable medical device is inserted therein for compression into a smaller diameter size. A directed light source 78 is positioned near the collet opening allows the operator to easily view placement of the stent in the chamber. Liquid nitrogen is poured into the Dewar vessel 40 via liquid nitrogen line 22 whereas nitrogen gas line 24 can be used for evacuating the liquid nitrogen gas.

FIG. 3C is an enlarged photograph of the interior of the loading chamber of FIG. 3A with a Leister heat gun 132 positioned near the DeWar jar 40 for heating the liquid nitrogen contained therein.

Set Up of Cooling Chamber 12

The set up of the cooling chamber is facilitated by the following:
1. Turn off all power to the box by shutting off the power strip at back of box and unplugging the Leister heat gun.
2. Remove tape from around viewing window access port and remove from box.

NOTE: Nitrile gloves, smock & facemask must be worn when cleaning cooling box.
3. Remove all tools and liquid nitrogen vessel making sure to wipe down with lint-free cloth and ethyl alcohol as removed. Be sure to remove the pusher cannula with force gauge adapter assembly from the force gauge and the box.
4. Wipe off access tubes, glove access cap and air lock caps and install all air lock caps.
5. Clean box as follows: cooling box must be cleaned with a lint-free cloth and ethyl alcohol. Use overlapping motions, start with the furthest point away from your body and wipe in one direction towards your body. Change wipes when starting with a new wall.
6. Wrap a cleaning wipe around the 5 GRW cannula so the wipe extends past the end of the cannula slightly, open fixture and using ethyl alcohol wipe out the inside of the fixture. Make sure the end of the cannula does not dig into the fixture when cleaning.
7. Change nitrile gloves.
8. Insert pusher cannula with force gauge adapter assembly, threaded end first into the fixture until the threaded end contacts the force gauge. Screw the assembly into the force gauge until a slight resistance is felt. Replace seal around pusher cannula.

NOTE: Take care that the pusher cannula with force gauge adapter assembly does not scratch the fixture.
9. Wipe down all loading tools, glove and appropriate container for liquid nitrogen and put back in cooling box.
10. Plug in Leister heat gun and start airflow by turning on bottom button. Do not turn on heat.
11. Turn on power strip that starts fan.
12. Turn on microscope light and camera. Adjust light focusing onto compression fixture orifice.
13. Wipe down inside surface of viewing window access panels, install in opening and tape edges to seal.
14. Turn on nitrogen gas and flow meter, adjust flow to between 0.1 and 0.3 MPH.
15. Purge environment inside box with nitrogen gas for 5 minutes.
16. Turn on temperature read-out gauge. Confirm gauge is set on k setting for thermocouple. If temperature is unstable, change battery.
17. After purging box, turn on liquid nitrogen approx. ½ turn.
18. Increase or decrease flow of liquid nitrogen to maintain liquid in the containment vessel without overflow until the temperature has reached 5 Degrees F.

NOTE: Flow meter will read at a higher MPH after turning on liquid nitrogen.
19. Remove cap and fill the access tube with stents in test tubes and appropriate length inner support cannula assemblies. Place cap back on the tube outside of the box.
20. Remove cap outside of box and position loaded stent catch bag on outlet tube exit. Make sure bag is sealed and has label with: stent size, batch no., and quantity. Order number must be on the bag if applied directly to an order.
21. Turn off liquid nitrogen.
22. Turn on force gauge and set indicator at 0. Confirm force gauge is in starting position.

FIG. 1A depicts the method steps 110-122 of loading a coated nitinol stent 66 into a transfer tube 94. The individual steps including each of these method steps is detailed as follows:
1. Verify temperature in cooling box is between −15 degrees and +5 degrees.
2. If temperature starts to warm up or liquid nitrogen gets low, refill liquid nitrogen Dewar vessel as required.
3. Put on non-latex glove.
4. Place hand with non-latex glove into inverted glove sleeve at access port and pull the cuff of the non-latex glove over the cuff of the glove sleeve. Hand may now be placed in box.
5. Remove air lock cap from glove access port and place on top of stent compression fixture.
6. Remove cap from access tube and remove test tubes with stents from access tube. Replace cap of access tube.
7. Remove cap from test tube and partially expose stent. Place test tube with partially exposed stent into holding rack. IMPORTANT—Only remove one stent from a test tube at a time to insure trackability. Each test tube is numbered.
8. With 0.040" stylet wire dip stent in liquid nitrogen. After dipping of stent, be careful not to bump stent as this could cause stent deformity.
9. With 0.040" stylet wire place stent completely in stent compression fixture. There should be approx. ¼" from end of stent to opening in fixture.
10. Close stent compression fixture with air cylinder and remove 0.040" stylet wire.
11. Insert inner support cannula assembly or support mandril in stent with cannula end first. Cannula of assembly should be located between gold rivets at both ends of the stent.
12. To insure proper positioning of inner support cannula, adjust the fixture hole size. Turning the adjustment knob counter clockwise while moving the support cannula back and forth does this. Continue this until the support cannula stops against the gold rivets at both ends. Adjustment knob is located with air cylinder on the outside bottom of cooling box.

13. Adjust a medium drag on support cannula by turning the adjust knob Counter clockwise. After sufficient drag is determined position support cannula by rivets farthest from exit opening.

NOTE: Transfer tube must be smooth on distal end to enable advancement of transfer tube assist tool.

14. Place transfer tube alignment cannula on inner support cannula. Transfer tube alignment cannula must butt up to stent. Place transfer tube onto transfer tube alignment cannula up to stent compression fixture opening. Advance large end of transfer tube assist tool over transfer tube.
15. Hold transfer tube assist tool against stent compression fixture and push stent into transfer tube by advancing force gauge.
16. Remove stent in transfer tube, transfer tube alignment cannula, transfer tube assist tool and inner support cannula from stent compression fixture.
17. Remove transfer tube assist tool from transfer tube.
18. Remove transfer tube alignment cannula from transfer tube.
19. Remove inner support cannula assembly by holding it against inside bottom of box (opposite end of flare on transfer tube) and push slightly until gold rivets slightly release from transfer tube. Remove inner support cannula assembly from stent.
20. Put stent in transfer tube back into test tube and replace cap. Place test tube into access tube with stent catch bag attached.
21. Turn adjustment knob on air cylinder clockwise to loosen fixture and release pressure on pusher cannula with force gauge adapter.
22. Open stent compression fixture using air cylinder and retrace force gauge and pusher cannula with force gauge adapter.
23. Send stents in sealed bag to area where they will be Quality Controlled and transferred into delivery systems.

Figure 4:
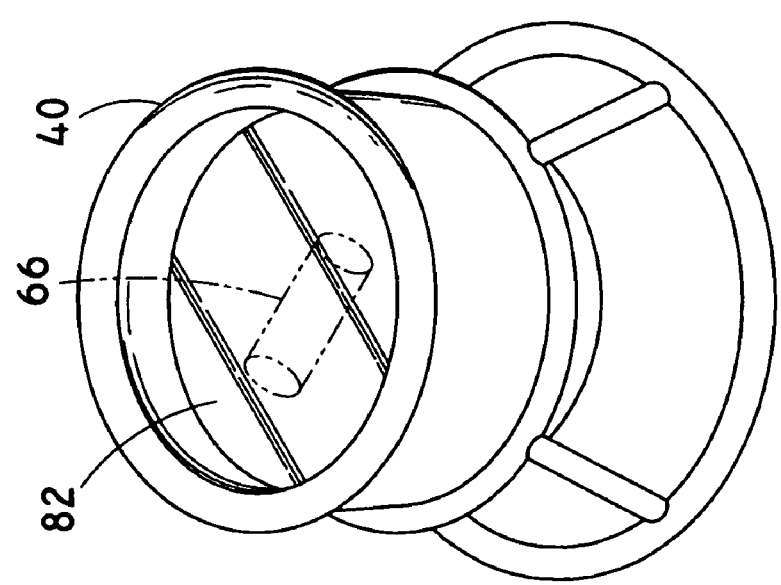
FIG. 4 is an enlarged pictorial view of the Dewar vessel of FIG. 3B in which the expandable medical device is placed therein for cooling.

FIG. 4 is an enlarged pictorial view of Dewar vessel 40 of FIG. 3B in which the expandable medical device or stent 66 is placed in liquid nitrogen 82 for cooling thereof.

Figure 5:
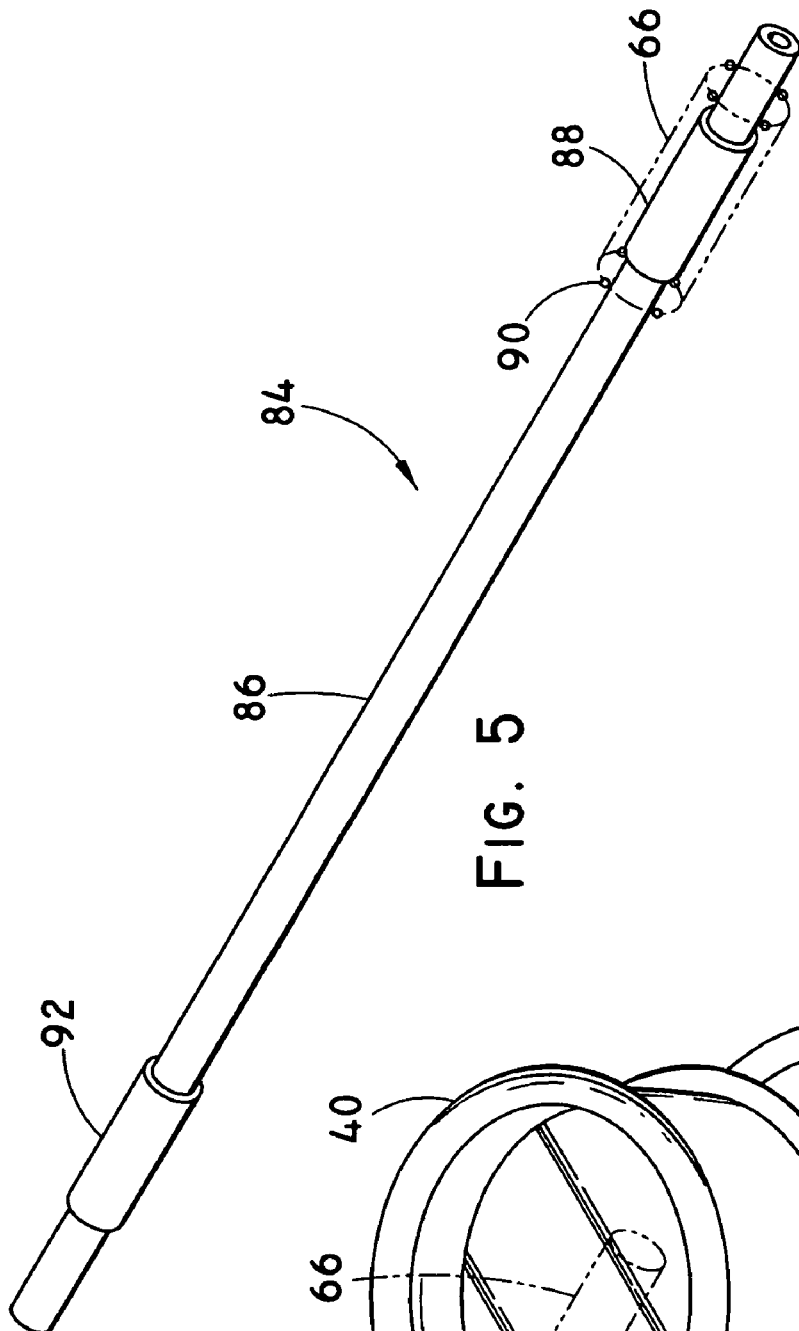
FIG. 5 is a pictorial diagram of the loading apparatus (support mandril) of FIG. 1C of which the expandable medical device is positioned thereon for insertion into the compressor.

FIG. 5 is a pictorial diagram of the apparatus such as support mandril 84 for positioning stent 66 about enlarged end 88 of the main body 86 of the mandril. The handle end 92 of the support mandril 84 is depicted at the opposite end thereof. Gold dot markers 90 are shown depicted on each end of the expandable stent 66.

Figure 6:
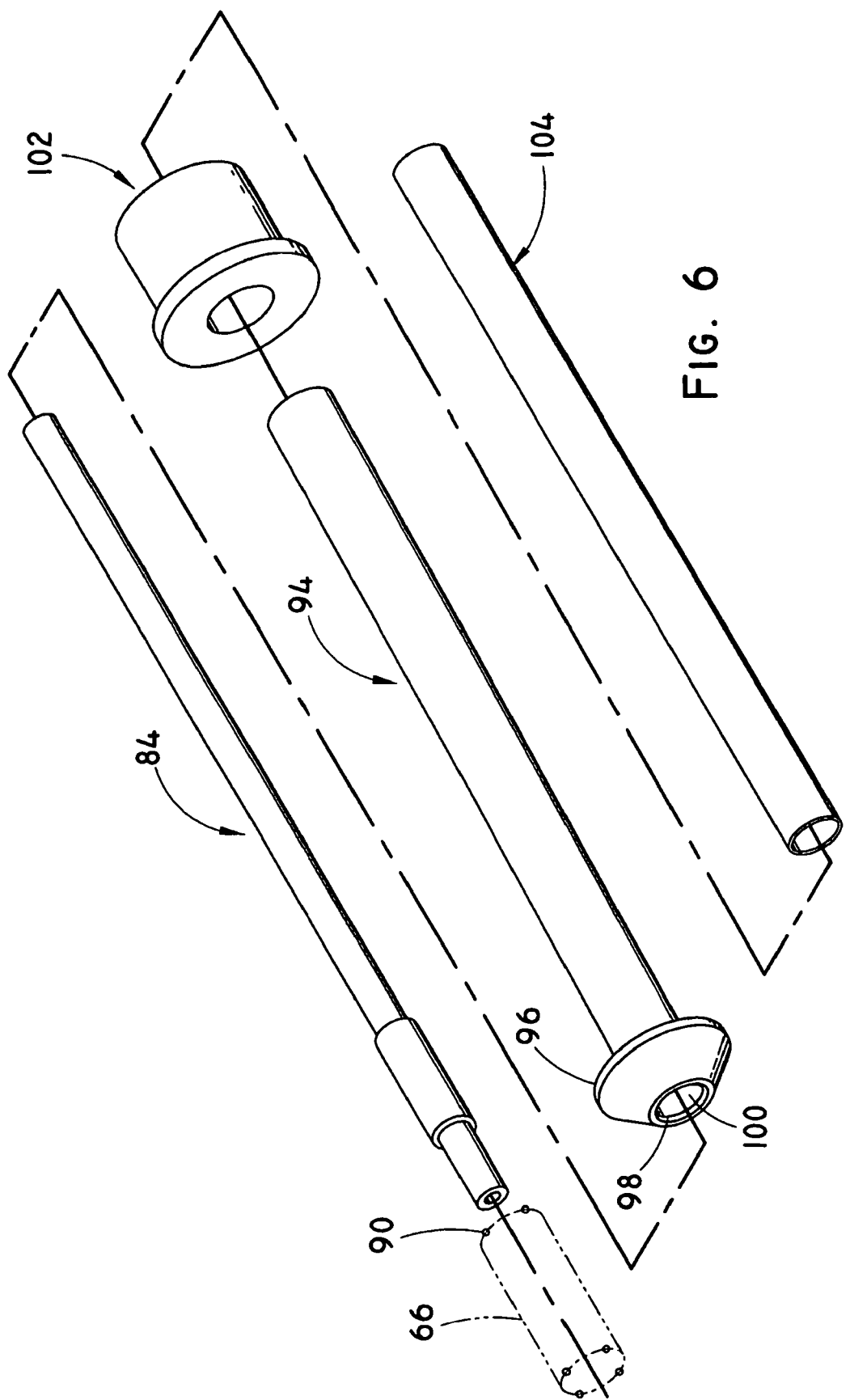
FIG. 6 is a pictorial assembly diagram of the components of the mandril for the positioning and compressing of the expandable medical device into the compressor of FIG. 1C.

FIG. 6 is a pictorial assembly diagram of the components of support mandril 84 for positioning in transfer tube 94 with lumen 100 extending longitudinally therethrough. One end 96 of transfer tube 94 is flared with a chamfer 98 on the flared loading end of the tube. A push bushing 102 slides over the other end of the transfer tube and an extraction support rod 104 is positioned inside transfer tube 94.

FIG. 7 depicts an expanded medical device 66 of the present invention inserted into collet opening 80 of the stent compressor 38 with the use of support mandril 84. The support mandril 84 is inserted into the lumen of the expanded stent 66 for compression around the expanded end 88 of the support mandril. When the enlarged end 88 of the support mandril is positioned in the lumen of stent 66, the stent compressor 38 is actuated by movement of stent compressor actuator 36. Stent compressor 38 is commercially available from Machine Solutions of Flagstaff, Ariz.

FIG. 8 depicts the compression of the stent by stent compressor 38 with support mandril 84 extending from collet compressed opening 106.

Figure 9:
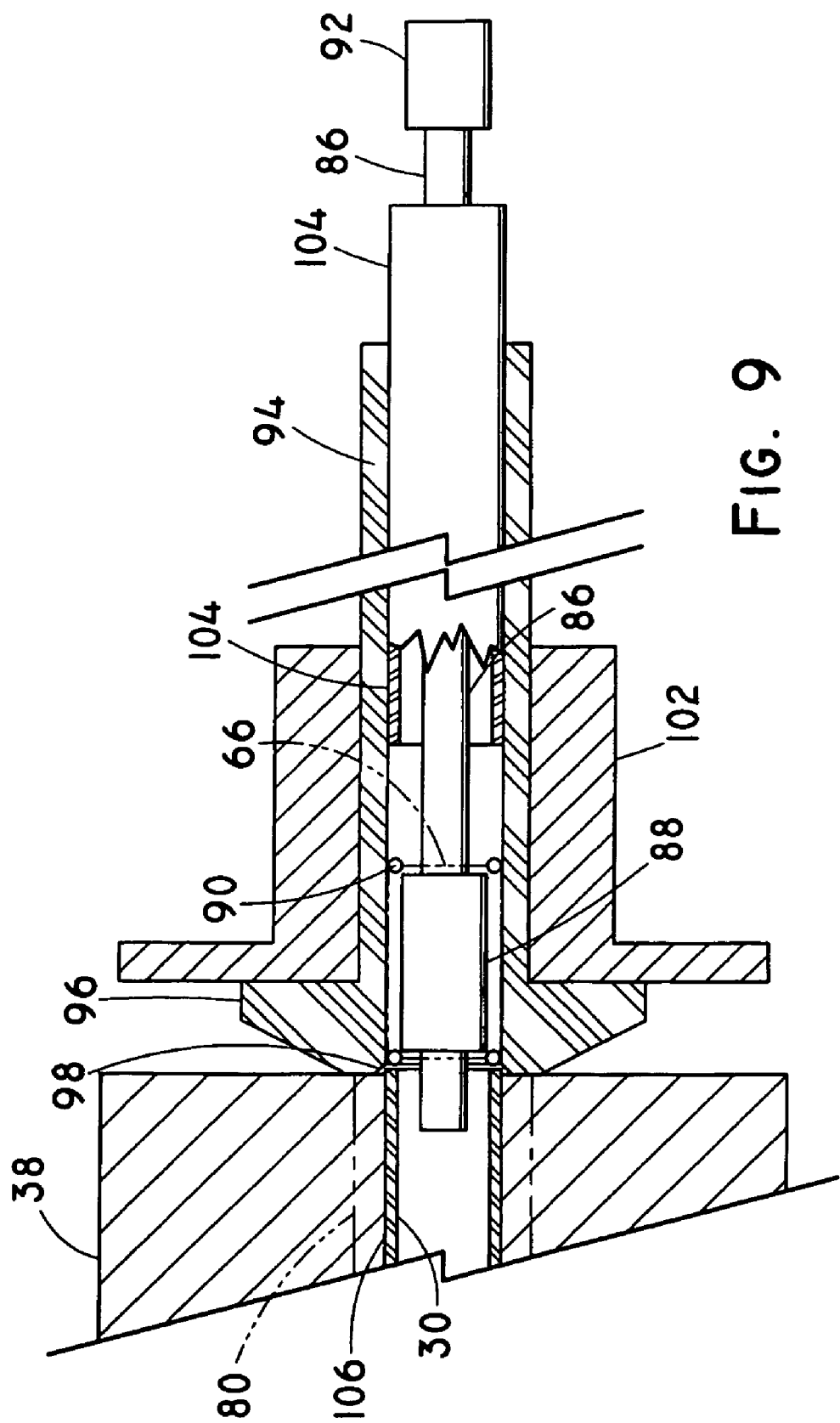
FIG. 9 depicts a partially sectioned diagram of the expandable medical device of the present invention on the support mandril being inserted into the aperture of the compressor of FIGS. 7 and 8.

FIG. 9 depicts a partially sectioned diagram of the expandable medical device 66 of the present invention positioned on the enlarged end 88 of the support mandril with pusher cannula 30 inside compressor 38 engaging one end of the stent with the other end of the stent for positioning against extraction support rod 104. The transfer tube 94 has a flared end 96 with chamfer 98 thereon for the loading of the flared end into the compressor. Push bushing 102 is utilized as shown for centering the support mandril and loaded stent 88. Pusher cannula 30 pushes the stent 66 into transfer tube 94. Extraction support rod 104 engages the other end of the stent when enlarged end 88 of the mandril is withdrawn from the lumen of the stent 66 just barely making contact with gold markers 90.

Figure 10:
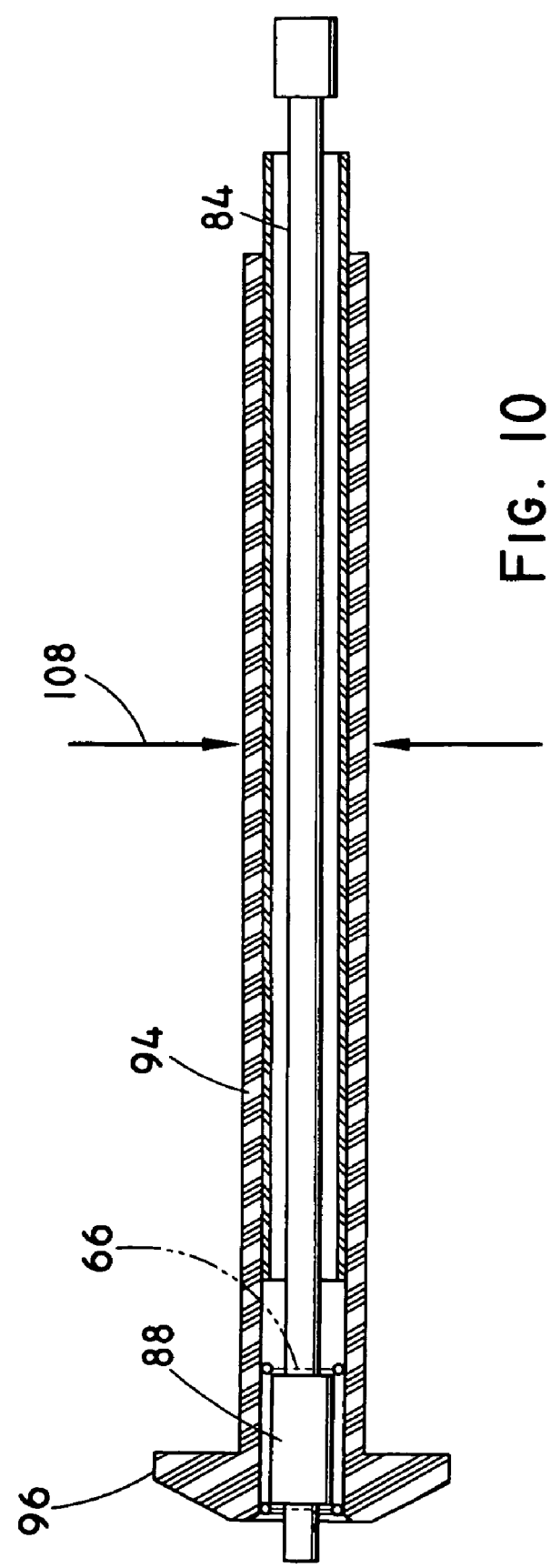
FIG. 10 depicts a section diagram showing removal of the support mandril from the insertion assembly.

FIG. 10 depicts a section detail showing removal of the mandril from the insertion assembly.

Instructions for Shutting Cooling Box Off
1. Turn off liquid nitrogen.
2. Turn on heat from Leister heat gun, top button.
3. Let cooling box heat up to 70 degrees F.
4. Shut off heat. Let fan run approx. 5 minutes, then shut off.
5. Shut off gas flow from liquid nitrogen tank.
6. Turn off temperature read out gauge and flow meter.
7. Turn off power strip.

Provided is a listing of assembly components for loading an expandable medical device into a transfer tube.

| LISTING OF ASSEMBLY COMPONENTS FOR LOADING AN EXPANDABLE MEDICAL DEVICE INTO A TRANSFER TUBE | |
|---|---|
| 10 | device |
| 12 | cooling chamber |
| 14 | access door |
| 16 | nitrogen source |
| 18 | nitrogen gas valve |
| 20 | nitrogen liquid valve |
| 22 | liquid N line |
| 24 | N gas line |
| 26 | thermometer |
| 28 | thermometer lead |
| 30 | pusher cannula |
| 32 | cannula pusher device |
| 34 | stent compressor actuater cyl. |
| 36 | stent compressor actuater |
| 38 | stent compressor |
| 40 | Dewar Vessel |
| 42 | light generator |
| 44 | fiber optic |
| 46 | stent container access tube |
| 48 | stent container delivery tube |
| 50 | gas evacuation access |
| 52 | gas evacuator |
| 54 | heated air port |
| 56 | air heater |
| 58 | manipulator access |
| 60 | actuating control valve |
| 62 | actuator valve lever |
| 64 | pusher valve lever |
| 66 | stent |
| 68 | pusher valve |
| 70 | pusher valve line |
| 72 | actuator valve line |
| 74 | actuating operating controls |
| 76 | manipulator device |
| 78 | directed light source |

-continued

LISTING OF ASSEMBLY COMPONENTS FOR LOADING
AN EXPANDABLE MEDICAL DEVICE INTO A TRANSFER TUBE

| | |
|---|---|
| 80 | collet opening |
| 82 | liquid N |
| 84 | support mandril |
| 86 | body of mandril |
| 88 | enlarged end of mandril |
| 90 | gold dot markers |
| 92 | handle end of 84 |
| 94 | transfer tube |
| 96 | flared end of 94 |
| 98 | chamfer on loading end of 96 |
| 100 | lumen of 94 |
| 102 | push bushing |
| 104 | extraction support rod |
| 106 | collet compressed opening |
| 108 | comp. To retain 104 in 94 |
| 110 | method block diagram |
| 112 | method of loading |
| 114 | placing in chamber |
| 116 | removing impurities |
| 118 | lowering temperature |
| 120 | compressing the stent |
| 122 | loading the stent |
| 124 | force gauge |
| 126 | seal |
| 128 | end cap |
| 130 | end cap |
| 132 | Leister heat gun |

What is claimed is:

1. A method of loading an expandable medical device in a low vapor environment, comprising the steps of:
   placing an expandable medical device in a chamber at a first temperature,
   removing from the chamber at least one of a vapor and any other impurities that can form at least one of a liquid and a solid on the medical device,
   lowering the temperature in the chamber to a temperature below a transition temperature of the medical device,
   compressing the medical device at a temperature below a transition temperature of the medical device, and
   loading the compressed medical device into at least one of a delivery device and a transfer device.

2. The method of claim 1, wherein the step of removing at least one of the vapor and any other impurities includes the step of purging the chamber with a gas for at least a prescribed period of time.

3. The method of claim 1, wherein the step of lowering the temperature in the chamber includes the step of lowering the temperature at a rate slow enough to remove the at least one of the vapor and any other impurities before condensation or sublimation thereof.

4. The method of claim 1, wherein the step of lowering the temperature in the chamber includes introducing liquid nitrogen into the chamber, heating the liquid nitrogen to produce nitrogen gas, and lowering the temperature in the chamber with the nitrogen gas.

5. The method of claim 1, further comprising the step of inserting the medical device in a compression fixture.

6. The method of claim 5, wherein the step of compressing includes the steps of inserting the medical device at a temperature below the transition temperature of the device into the compression fixture and compressing the medical device with a first diameter to a second diameter less than the first diameter.

7. The method of claim 1, wherein the step of removing at least one of the vapor and any other impurities includes the step of purging the chamber with a gas for at least a prescribed period of time and wherein the step of lowering the temperature in the chamber includes the step of lowering the temperature at a rate slow enough to remove the at least one of the vapor and any other impurities before condensation or sublimation thereof.

8. The method of claim 7, wherein the step of lowering the temperature in the chamber further includes the steps of introducing liquid nitrogen into the chamber, heating the liquid nitrogen to produce nitrogen gas, and lowering the temperature in the chamber with the nitrogen gas.

9. The method of claim 8, further comprising the step of inserting the medical device in a compression fixture.

10. The method of claim 9, wherein the step of compressing includes the steps of inserting the medical device at a temperature below the transition temperature of the device into the compression fixture and compressing the medical device with a first diameter to a second diameter less than the first diameter.

* * * * *